United States Patent

Burns

[11] Patent Number: 5,100,381
[45] Date of Patent: Mar. 31, 1992

[54] ANGIOPLASTY CATHETER

[75] Inventor: Matthew M. Burns, Minneapolis, Minn.

[73] Assignee: SciMed Life Systems, Inc., Maple Grove, Minn.

[21] Appl. No.: 586,380

[22] Filed: Sep. 20, 1990

Related U.S. Application Data

[63] Continuation of Ser. No. 337,319, Apr. 17, 1989, abandoned.

[51] Int. Cl.⁵ .................................. A61M 25/00
[52] U.S. Cl. .................................. 604/96; 604/103; 606/194
[58] Field of Search .............. 604/96, 103, 264, 280, 604/281, 282; 606/191–194

[56] References Cited

U.S. PATENT DOCUMENTS

| | | | |
|---|---|---|---|
| 4,456,000 | 6/1984 | Schjeldahl et al. | 604/194 |
| 4,496,345 | 1/1985 | Hasson | 604/103 |
| 4,573,470 | 3/1986 | Samson et al. | 604/96 |
| 4,597,755 | 7/1986 | Samson et al. | 604/96 |
| 4,646,742 | 3/1987 | Packard et al. | 606/194 |
| 4,729,914 | 3/1988 | Kliment et al. | 428/36 |
| 4,762,129 | 8/1988 | Bonzel | 606/194 |
| 4,798,586 | 1/1989 | Stevens | 604/96 |
| 4,819,751 | 4/1989 | Shimada et al. | 606/196 |
| 4,820,349 | 4/1989 | Saab | 604/96 |
| 4,846,174 | 7/1989 | Willard et al. | 604/96 |
| 4,877,031 | 10/1989 | Conway et al. | 604/96 |
| 4,896,670 | 1/1990 | Crittenden | 606/194 |
| 4,906,241 | 3/1990 | Roddin et al. | 606/194 |
| 4,917,088 | 4/1990 | Crittenden | 606/194 |
| 4,921,483 | 5/1990 | Wiljay et al. | 604/96 |
| 4,943,278 | 7/1990 | Euteneuer | 604/96 |
| 4,946,466 | 8/1990 | Pinchuk et al. | 606/194 |
| 4,964,409 | 10/1990 | Tremulis | 128/657 |
| 4,976,690 | 12/1990 | Solar et al. | 606/194 |
| 4,998,923 | 3/1991 | Samson et al. | 606/194 |

FOREIGN PATENT DOCUMENTS

| | | | |
|---|---|---|---|
| 0279958 | 8/1988 | European Pat. Off. | 604/280 |
| 8902763 | 4/1989 | PCT Int'l Appl. | 604/208 |
| 2130093 | 5/1984 | United Kingdom | 604/264 |

*Primary Examiner*—Stephen C. Pellegrino
*Assistant Examiner*—Ralph A. Lewis
*Attorney, Agent, or Firm*—Kinney & Lange

[57] ABSTRACT

An over-the-wire balloon catheter for use in angioplasty includes a dual lumen shaft formed by a multisection outer tube and a multisection inner tube. The outer tube includes a first thin wall outer tube section which is connected to a manifold at its proximal end. The outer tube also includes a second outer tube section which is attached to the distal end of the first outer tube section and which has a greater flexibility. The inner tube has a first thin wall inner tube section which extends generally coaxially through the first outer tube section and into the interior of the second outer tube section. The inner tube also includes a second thin wall inner tube section which is attached to the distal end of the first inner tube section and extends distally beyond the distal end of the outer tube. A balloon is attached to the distal ends of the outer and inner tubes. The inner tube sections have a coating of a low friction material, such as polyimide-polytetrafluoroethylene composite, on their inner walls to facilitate movement of a guide wire through the guide wire lumen of the inner tube.

43 Claims, 1 Drawing Sheet

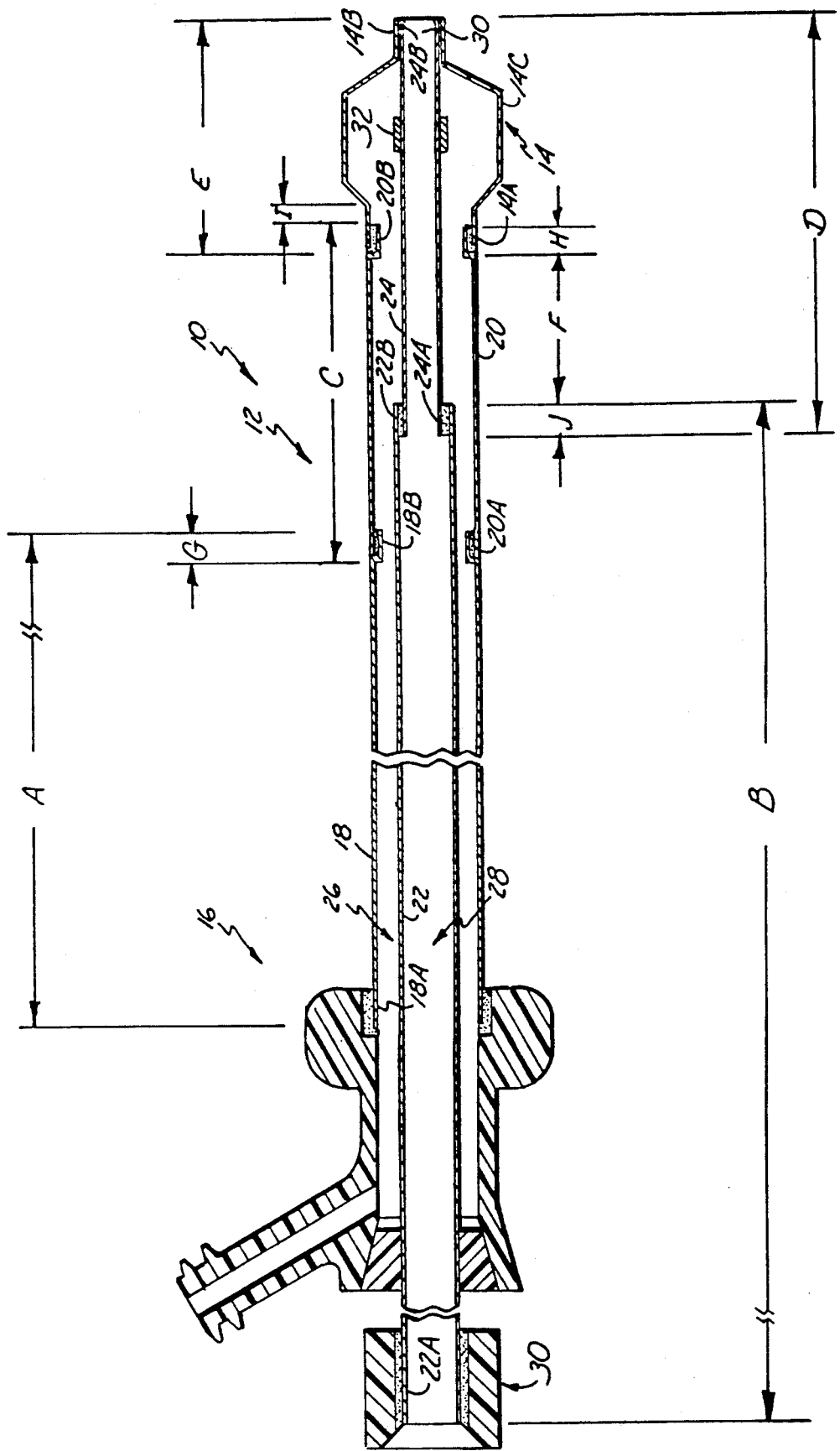

ANGIOPLASTY CATHETER

This is a continuation of application Ser. No. 07/337,319 filed on Apr. 13, 1989, abandoned as of the date of this application.

BACKGROUND OF THE INVENTION

1. Field of the Invention

The present invention relates to the field of angioplasty. In particular, the present invention relates to a dilatation balloon catheter of the "over-the-wire" type.

2. Description of the Prior Art

Angioplasty has gained wide acceptance in recent years as an efficient and effective method for treating types of vascular disease. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Typically, a hollow guide catheter is used in guiding the dilatation catheter through the vascular system to a position near the stenosis (e.g. to the aortic arch). Using fluoroscopy, the physician guides the dilatation catheter the remaining distance through the vascular system until the balloon is positioned across the stenosis. The balloon is then inflated by supplying a fluid under pressure through an inflation lumen to the balloon. The inflation of the balloon causes stretching of the artery and pressing of the lesion into the artery wall to reestablish acceptable blood flow through the artery.

There has been a continuing effort to reduce the profile and shaft size of the dilatation catheter so that the catheter not only can reach but also can cross a very tight stenosis. A successful dilatation catheter must also be sufficiently flexible to pass through tight curvatures, especially in the coronary arteries. A further requirement of a successful dilatation catheter is its "pushability". This involves the transmission of longitudinal force along the catheter from its proximal end to its distal end so that a physician can push the catheter through the vascular system and the stenosis.

Two commonly used types of dilatation catheters are referred to as "over-the-wire" catheters and "non-over-the-wire" catheters. An over-the-wire catheter is one in which a separate guide wire lumen (sometimes called a "thru lumen") is provided so that a guide wire can be used to establish the path through the stenosis. The dilatation catheter can then be advanced over the guide wire until the balloon is positioned within the stenosis. One problem with the over-the-wire catheter is the requirement of a larger profile and a generally larger outer diameter along its entire length in order to allow for a separate guide wire lumen.

A non-over-the-wire catheter acts as its own guide wire, and thus there is no need for a separate guide wire lumen. One advantage of a non-over-the-wire catheter is its potential for a reduced outer diameter along its main shaft since a guide wire lumen is not required. However, one disadvantage is the inability to maintain the position of a guide wire within the vascular system when removing the catheter and exchanging it for one of a smaller (or larger) balloon diameter. Thus, to accomplish an exchange with the non-over-the-wire catheter, the path to the stenosis must be reestablished when replacing the catheter with one having a different balloon diameter.

It is desirable in some cases to feed two dilatation catheters through the same guide catheter simultaneously. This procedure is used, for example, to inflate both sides of a Y branch in the coronary arteries. In the past, only non-over-the-wire catheters have been small enough to be used for this type of procedure. In general, the need for providing two lumens in an over-the-wire catheter has resulted in a larger outer diameter along its entire length so that it is not possible to feed two over-the-wire catheters through a typical 8 French (8F) guide catheter at the same time.

SUMMARY OF THE INVENTION

The present invention is an improved over-the-wire dilatation catheter which uses a multisection outer tube and a multisection inner tube to achieve a very small outer diameter, so that two such dilatation catheters can be fed through the same guide catheter simultaneously.

The present invention makes use of a multisection outer tube and a multisection inner tube with a balloon attached to the distal ends of the inner and outer tubes. An inflation lumen is formed between the outer wall of the inner tube and the inner wall of the outer tube. A guide wire or through lumen extends through the interior of the inner tube.

The outer tube has a first (or proximal) thin wall tube section and a second (or distal) tube section. The distal outer tube section has a greater flexibility than the proximal outer tube section to allow the catheter to be advanced through the rather tortuous paths of the coronary arteries.

The inner tube has a proximal thin wall tube section and a distal thin wall tube section. The proximal and distal inner tube sections are joined together within the interior of the distal outer tube section. The distal inner tube section has a smaller inner and outer diameter than the proximal inner tube section. The inner tube's inner diameter surfaces are defined as a lubricious surface in order to facilitate relative movement of the catheter and the guide wire.

In the preferred embodiments of the present invention, the proximal outer tube section is a stainless steel hypotube or a polyimide tube, and the distal outer tube section is a high density polyethylene tube. The proximal inner tube section is preferably a stainless steel hypotube with a lubricious inner diameter surface of polytetrafluoroethylene, or a polyimide tube with a lubricious inner diameter surface of polyimide-polytetrafluoroethlyene composite material. The distal inner tube section is preferably a polyimide tube with a lubricious inner diameter surface of polyimide-polytetrafluoroethylene composite material.

BRIEF DESCRIPTION OF THE DRAWINGS

The FIGURE is a sectional view of the dilatation balloon catheter of the present invention.

DETAILED DESCRIPTION OF PREFERRED EMBODIMENTS

Dilatation balloon catheter 10 shown in the FIGURE is a coaxial dual lumen dilatation catheter which offers a very small outer diameter—preferably small enough so that two similar catheters can be fed simultaneously through an 8 French (8F) guide catheter. Dilatation balloon catheter 10 is formed by a multilumen shaft 12 which has an inflatable balloon 14 mounted at its distal end and a manifold 16 mounted at its proximal end.

Shaft 12 includes a multisection outer tube (formed by proximal outer tube section 18 and distal outer tube section 20) and a multisection inner tube (formed by proximal inner tube section 22 and distal inner tube section 24). Inflation lumen 26 is defined between the outer walls of inner tube sections 22 and 24 and the inner walls of outer tube sections 18 and 20. Inflation lumen 26 extends from manifold 16 to the interior of balloon 14. Guide wire (or thru) lumen 28 extends through the interior of inner tube sections 22 and 24 from manifold 16 to distal opening 30 at the distal end of catheter 10.

Proximal outer tube section 18 has its proximal end 18A connected to manifold 16 and its distal end 18B bonded to proximal end 20A of distal outer tube section 20. Distal end 20B of distal outer tube section 20 is bonded to proximal waist section 14A of balloon 14.

Inner tube section 22 has a proximal end 22A which extends proximally beyond proximal end 18A of outer tube section 18, through manifold 16 and which is connected to a thru lumen adapter 30. At distal end 22B, inner tube section 22 is connected to proximal end 24A of inner tube section 24. In a preferred embodiment, the connection between inner tube sections 22 and 24 is distal of the distal end 18B of the proximal outer tube section 18. Distal end 24B of inner tube section 24 is bonded to distal section 14B of balloon 14.

Balloon 14 has an intermediate, inflatable section 14C located between proximal segment 14A and distal segment 14B. The interior of balloon 14 is in communication with inflation lumen 26. In the FIGURE, balloon 14 is shown in its inflated condition.

In order to achieve a very small outer diameter, while retaining the necessary pushability and flexibility characteristics and the ability to handle high inflation pressures, tube sections 18, 20, 22 and 24 are thin wall, high strength tubing. In a preferred embodiment of the present invention, proximal outer tube section 18 is a stainless steel hypotube or polyimide thin wall tube. The term "thin wall" as used in this application means a wall thickness of less than 0.002 inches and preferably on the order of 0.001 inches or less. Stainless steel hypotube and polyimide tubing are desireable because they offer the advantages of a thin wall construction with the necessary strength to achieve the needed pushability and with high burst pressure rating.

In a preferred embodiment, proximal inner tube section 22 also is a polyimide tube or a stainless steel hypotube having a thin wall construction. In either case, the inner surface of the inner tube section 22 is composed of a low friction, lubricious material. In a preferred embodiment, a hydrophobic material such as a polyimide-polytetrafluoroethylene composite has been found to be desireable because it provides for a low friction inner surface that allows free guide wire movement (axial and torsional) in and thru lumen 28, despite very small clearances. When a stainless steel hypotube is employed as the inner tube section 22, a preferred inner surface coating is a hydrophobic such as tetrafluoroethylene. In a further embodiment, the desired lubricity can be obtained by use of a hydrophilic coating material such as a polyacrylamide polyurethane substrate.

Distal outer tube section 20 is, in a preferred embodiment, high density polyethylene having a wall thickness of approximately 0.0025 inches. The high density polyethylene tubing has greater flexibility than either stainless steel hypotube or polyimide tubing which form proximal outer tube section 18. This greater flexibility allows the distal end of catheter 10 to be guided through the tortuous passage of the coronary artery. Less flexibility is required for proximal section 18 and, instead, pushability is the more important characteristic.

The material selected for distal outer tube section 2 must offer relatively small wall thickness together with the appropriate level of flexibility and a relatively high burst pressure. High density polyethylene tubing, with a wall thickness of about 0.0025 inches, has been found to have these desired characteristics.

A lubricious outer surface is desired for both sections of the outer tube. The outer tube sections may be formed from a lubricious material, or coated with a lubricious material. For a stainless steel or polyethylene tube, a preferred lubricious coating is a hydrophobic material such as a polytetrafluoroethylene, while for a polyimide tube, a preferred lubricious coating is a hydrophobic material such as a polyimide-polytetrafluoroethylene composite. In a further embodiment, the desired lubricity is attained by use of a hydrophilic material such as a polyacrylamide polyurethane substrate.

Distal inner tube section 24 is preferable a polyimide tube with a hydrophobic lubricious material, such as a polyimide-polytetrafluoroethylene composite low friction material, on its inner surface (alternatively, the desired lubricity is attained by use of a hydrophilic coating material such as a polyacrylamide polyurethane substrate). The polyimide tube forming distal inner tube section 24 has a thin wall tube and has a smaller inner and outer diameter than the proximal inner tube section 22. As a result, distal inner tube section 24 has a greater flexibility than proximal inner tube section 22, which also helps overall flexibility of the distal end of catheter 10.

The material selected for inner tube sections 22 and 24 must have sufficient strength, even in a thin wall construction, to resist collapse when fluid pressure is applied through inflation lumen 26 to the interior of balloon 14. Both polyimide tubing and stainless steel hypotube offer sufficient strength against collapse with the fluid pressures typically used to inflate balloon 14.

Balloon 14 is, in one preferred embodiment, a polyolefin balloon. In other embodiments of the present invention, balloon 14 is a polyimide balloon.

In the preferred embodiment of the present invention seen in the FIGURE, one or more radiopaque markers 32 are provided on the distal inner tube section 24, preferably within the area bounded by the balloon 14. Such markers are provided to aid in inserting and locating the catheter by fluoroscopy in the patient's vascular system during angioplasty.

In one preferred embodiment of the present invention, which yields an overall outer diameter of 0.033 inches, proximal outer tube section 18 is a hypotube having an inner diameter of 0.028 inches and an outer diameter of 0.0320 inches, with a polytetrafluoroethylene outer surface (for lower surface tension) with wall thickness of approximately 0.0005 inches. Distal outer tube section 20 is a high density polyethylene tube having an outer diameter of 0.033 inches and an inner diameter of 0.028 inches. Proximal inner tube section 22 is a polyimide tube having an outer diameter of 0.0200 inches and an inner diameter of 0.0175 inches. A polyimidepolytetrafluoroethylene composite material covers the inner surface of tube sections 22 and 24. Distal inner tube section 24 is a polyimide tube having an outer diameter of 0.014 inches and an inner diameter of 0.012 inches.

In the FIGURE, the lengths of various portions of catheter 10 are labeled. A is the length of proximal outer tube section 18 (including bonds). B is the length of proximal inner tube section 22 (including bonds). C is the length of distal outer tube section 20 (including bonds). D is the length of distal inner tube section 24 (including bonds). E is the length of balloon 14. F is the distance from the distal end of inner tube section 22 to the proximal end of balloon 14. G is the length of the bond between outer tube sections 18 and 20. H is the length of the bond between outer tube section 20 and balloon 14. I is the length of the balloon waist between the distal end of outer tube section 20 and inflatable section 14 of balloon 14. J is the length of the bond between inner tube sections 22 and 24.

In the preferred embodiment of the present invention which provided an outer diameter of 0.033 inches, the following dimensions were used:

| | |
|---|---|
| A = 42.34 inches | F = 5.48 inches |
| B = 50.39 inches | G = 0.12 inches |
| C = 12.24 inches | H = 0.12 inches |
| D = 7.12 inches | I = 0.12 inches |
| E = 1.4 inches | J = 0.12 inches |

This preferred embodiment of the catheter 10 of the present invention is typically used in conjunction with a guide wire having a distal segment of about 12 inches in length and an outer diameter of 0.010 inches. The proximal section of the guide wire must have a length greater than length B shown in the drawing, and in preferred embodiments has an outer diameter which ranges from 0.010 inches to about 0.014 inches.

By extending proximal inner tube section 22 into distal outer tube section 20, the length of distal inner tube section 24 (which has a smaller inner diameter) is shortened so that even a guide wire having a proximal section with an outer diameter which is too large to extend into distal inner tube section 24 can extend several inches beyond the distal end of the catheter 10 (e.g. up to about 5 or 6 inches). In the example of the preferred embodiment presented above, proximal inner tube section 22 extends approximately 6.64 inches into distal outer tube section 20 (C−(H+F)=6.64 inches).

In conclusion, the present invention takes advantage of the characteristics of high strength and thin wall tubing to achieve a smaller outer diameter dilatation catheter while retaining the advantages of an over-the-wire configuration. Although polyimide and stainless steel are two thin wall tubing materials which have been discussed in detail, other materials or combinations of materials can also be considered. For example, an alternative configuration for the inner tubing of catheter 10 is a multilayer tube having polyethylene on the inside and paralene on the outside. The polyethylene provides a lubricious surface to facilitate wire movement while the paralene provides structural strength which could not be achieved in a thin wall configuration with polyethylene alone. Another alternative would be to form the inner tube sections integrally from the same material.

Although the present invention has been described with reference to preferred embodiments, workers skilled in the art will recognize changes may be made in form and detail without departing from the spirit of the scope of the invention. For example, different sizes of balloons will have different section lengths (E, D and I), and different manifold constructions will result in different lengths (B) for the proximal inner tube section.

What is claimed is:

1. A dilatation catheter comprising:
    an inner tube including a first inner tube section and a second inner tube section connected together and having a guide wire lumen extending therethrough, the second inner tube section extending distally from the first inner tube section and having an outer diameter which is less than the outer diameter of the first inner tube section, the first and second inner tube sections having wall thicknesses less than about 0.002 inches and having a lubricious material on their inner surfaces;
    an outer tube positioned over the inner tube to define an inflation lumen between the inner tube and the outer tube, the outer tube having a first outer tube section having a wall thickness of less than about 0.002 inches and a second outer tube section positioned distally of the first outer tube section having a wall thickness of less than about 0.003 inches, the second outer tube section having greater flexibility than and made of material different than material of the first outer tube section; and
    a balloon having a proximal portion connected to a distal end of the second outer tube section and a distal portion connected to a distal end of the second inner tube section, the balloon being made of material different than material of the second outer tube section.

2. The dilatation catheter of claim 1 wherein the first inner tube section extends distally beyond a distal end of the first outer tube section.

3. The dilatation catheter of claim 1 wherein the first outer tube section is a thin wall metal tube.

4. The dilatation catheter of claim 3 wherein the first outer tube section is a stainless steel tube.

5. The dilatation catheter of claim 1 wherein the outer tube has a lubricious material as its outer surface.

6. The dilatation catheter of claim 5 wherein the lubricious materials as the outer surface of the outer tube is hydrophobic.

7. The dilatation catheter of claim 6 wherein the hydrophobic lubricious material is a polytetrafluoroethylene coating.

8. The dilatation catheter of claim 5 wherein the lubricious material as the outer surface of the outer tube is hydrophilic.

9. The dilatation catheter of claim 8 wherein the hydrophilic lubricious material is a polyacrylamide polyurethane substrate.

10. The dilatation catheter of claim 1 wherein the first outer tube section is a polyimide tube.

11. The dilatation catheter of claim 10 wherein the first outer tube section has a polyimide-polytetrafluoroethylene composite material as its outer surface for lubricity.

12. The dilatation catheter of claim 1 wherein the first inner tube section is a polyimide tube.

13. The dilatation catheter of claim 12 wherein the lubricious material is hydrophobic.

14. The dilatation catheter of claim 13 wherein the hydrophobic lubricious material is a polyimidepolytetrafluoroethylene composite.

15. The dilatation of claim 12 wherein the lubricious material is hydrophilic.

16. The dilatation of claim 15 wherein the hydrophilic lubricious material is a polyacrylamide polyurethane substrate.

17. The dilatation catheter of claim 1 wherein the first inner tube section is a metal tube.

18. The dilatation catheter of claim 17 wherein the lubricious material is hydrophobic.

19. The dilatation catheter of claim 18 wherein the hydrophobic lubricious material is a polyimidepolytetrafluoroethylene composite.

20. The dilatation catheter of claim 18 wherein the second outer tube is a polyethylene tube.

21. The dilatation catheter of claim 20 wherein the polyethylene second outer tube has an outer coating of a polyimide-polytetrafluoroethylene composite for lubricity.

22. The dilatation catheter of claim 17 wherein the lubricious material is hydrophilic.

23. The dilatation catheter of claim 22 wherein the hydrophilic lubricious material is a polyacrylamide polyurethane substrate.

24. The dilatation catheter of claim 1 wherein the second outer tube section is a high density polyethylene tube.

25. The dilatation catheter of claim 1 wherein the second inner tube section is a polyimide tube.

26. The dilatation catheter of claim 25 wherein the lubricious material is hydrophobic.

27. The dilatation catheter of claim 26 wherein the hydrophobic lubricious material is a polyimidepolytetrafluoroethylene composite.

28. The dilatation catheter of claim 25 wherein the lubricious material is hydrophilic.

29. The dilatation catheter of claim 28 wherein the hydrophilic lubricious material is a polyacrylamide polyurethane substrate.

30. The dilatation catheter of claim 1 wherein the first outer tube section is a metal tube, the first inner tube section is a polyimide tube having a polyimide-polytetrafluoroethylene composite material on an inner wall surface thereof, the second outer tube section is a high density polyethylene tube, and the second inner tube section is a polyimide tube having a polyimide-polytetrafluoroethylene composite material on an inner wall surface thereof.

31. The dilatation catheter of claim 1 wherein the balloon is a polyimide balloon.

32. A dilatation catheter comprising:

a first outer tube having a wall thickness of less than about 0.002 inches;
a first inner tube extending through the first outer tube, the first inner tube having a wall thickness of less than about 0.002 inches;
a second outer tube having proximal and distal ends, having greater flexibility than and made of material different than material of the first outer tube, and having its proximal end connected to a distal end of the first outer tube;
a second inner tube having proximal and distal ends, having a wall thickness of less than about 0.002 inches, and having an outer diameter which is less than an outer diameter of the first inner tube, the proximal end of the second inner tube being connected to a distal end of the first inner tube; and
a balloon having a proximal portion connected to the distal end of the second outer tube and a distal portion connected to the distal end of the second inner tube, the balloon being made of material different than material of the second outer tube.

33. The dilatation catheter of claim 32 wherein the first inner tube extends through the first outer tube and into the second outer tube.

34. The dilatation catheter of claim 32 wherein the first and second inner tubes have lubricious inner wall surfaces.

35. The dilatation catheter of claim 32 wherein the first and second inner tubes are polyimide tubes.

36. The dilatation catheter of claim 35 wherein the polyimide tubes have an inner wall of a polyimidepolytetrafluoroethylene composite material.

37. The dilatation catheter of claim 32 wherein the first outer tube is a metal tube.

38. The dilatation catheter of claim 32 wherein the first outer tube has an outer coating of polytetrafluoroethylene for lubricity.

39. The dilatation catheter of claim 32 wherein the first outer tube has an outer coating of a polyimide-polytetrafluoroethylene composite for lubricity.

40. The dilatation catheter of claim 32 wherein the first and second outer tubes have lubricious outer surfaces.

41. The dilatation catheter of claim 32 wherein the first inner tube is a metal tube.

42. The dilatation catheter of claim 41 wherein the metal tube has an inner coating of polytetrafluoroethylene for lubricity.

43. The dilatation catheter of claim 32 wherein the balloon is a polyimide balloon.

* * * * *